United States Patent
Coufal

(10) Patent No.: US 6,355,797 B2
(45) Date of Patent: Mar. 12, 2002

(54) PROCESS FOR COOLING MELAMINE

(75) Inventor: Gerhard Coufal, Leonding (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 09/791,615

(22) Filed: Feb. 26, 2001

Related U.S. Application Data

(63) Continuation of application No. 09/582,392, filed as application No. PCT/EP99/00353 on Jan. 20, 1999, now abandoned.

(30) Foreign Application Priority Data

Jan. 30, 1998 (AT) .............................................. 159/98

(51) Int. Cl.$^7$ ............................................ C07D 251/62
(52) U.S. Cl. ...................................... 544/201; 544/203
(58) Field of Search .................................. 544/201, 203

(56) References Cited

U.S. PATENT DOCUMENTS

| | | | |
|---|---|---|---|
| 4,465,832 A | 8/1984 | de Wit et al. | 544/201 |
| 4,565,867 A | 1/1986 | Thomas et al. | 544/201 |
| 5,514,796 A | 5/1996 | Best et al. | 544/201 |
| 5,721,363 A * | 2/1998 | Canzi et al. | 544/201 |

FOREIGN PATENT DOCUMENTS

| | | |
|---|---|---|
| WO | 95/01345 | 1/1995 |
| WO | 96/20182 | 7/1996 |
| WO | 96/20183 | 7/1996 |

* cited by examiner

Primary Examiner—Richard L. Raymond
Assistant Examiner—Venkataraman Balasubramanian
(74) Attorney, Agent, or Firm—Wenderoth, Lind & Ponack, LLP

(57) ABSTRACT

Process for cooling liquid melamine by mixing with solid melamine or with solid inert substances or with a mixture of solid melamine and solid inert substances.

19 Claims, No Drawings

PROCESS FOR COOLING MELAMINE

This is a continuation of U.S. patent application Ser. No. 09/582,392, filed Jun. 23, 2000, now abandoned, which is a 371 of PCT/EP99/00353, filed Jan. 20, 1999.

The application relates to a process for cooling liquid melamine by mixing with solid melamine.

The literature has already disclosed a multiplicity of processes for preparing melamine (Ullmann's Encyclopedia of Industrial Chemistry, 5th Edition, Vol. A-16, pp 174–179). All industrially important processes begin from urea, which is reacted to form melamine, ammonia and $CO_2$ either at high pressure and non-catalytically or at low pressure with the use of a catalyst.

In the low-pressure processes, gaseous melamine is produced, in the high-pressure processes, essentially liquid melamine is produced. Gaseous melamine present is passed, together with the off-gases $CO_2$ and $NH_3$, through a urea melt, with the off-gases cooling, the melamine dissolving in the urea and the urea being heated and fed to the reactor for the melamine synthesis. Gaseous melamine is also produced by the high-pressure process of WO 95/01345 (Kemira), the melamine melt finally obtained evaporating.

A big problem in the cooling and solidification of liquid melamine is that a temperature difference of over 300° C. must be passed through, and byproducts can form in the course of this. A familiar method for cooling is quenching with water or with steam, recrystallization generally being necessary in order to remove the various byproducts. If gas, for instance gaseous ammonia, is used for quenching, very high volumes of gas must be used and circulated. If liquid ammonia is used for quenching, for instance as in U.S. Pat. No. 4,565,867, although the heat of evaporation of the ammonia is used for cooling, likewise large amounts of gas must be circulated and continuously recompressed. Unexpectedly, a simple process has now been found in which the formation of byproducts is suppressed and in which large amounts of gas do not need to be circulated and recompressed.

The invention therefore relates to a process/ for cooling liquid melamine by mixing with solid melamine or with solid inert materials or with a mixture of solid melamine and solid inert materials.

Suitable solid inert materials can preferably be metal particles or glass particles, for example balls or rods of steel, in particular stainless steel, steel alloys or titanium alloys. It is also possible to cool additionally by feeding cold liquid $NH_3$ or gaseous $NH_3$ or by additional cooling elements and heat exchangers.

To mix the liquid melamine with solid melamine, not only can solid melamine be introduced into the liquid melamine, but also liquid melamine can be introduced into solid melamine, or the reaction partners encounter one another in a pressure-reduction and quenching vessel (quencher). It is preferable here if the liquid melamine is reduced in pressure on mixing. It is found to be advantageous to feed additional $NH_3$ during the mixing. The melamine is preferably cooled to below the melting point of melamine.

The liquid melamine to be cooled is under a certain ammonia pressure of about from 1 to 1000 bar. Since liquid melamine, depending on pressure and temperature, comprises byproducts such as melam, melem, melone, ureidomelamine, ammeline or ammelide, or has a tendency to eliminate $NH_3$, it is preferably under ammonia pressure. The higher this ammonia pressure, the lower the content of byproducts. Depending on the melamine preparation process carried out, the liquid melamine to be cooled is advantageously under an ammonia pressure of from about 40 to 1000 bar, preferably from about 40 to 400 bar, particularly preferably under a pressure of from about 60 to 300 bar.

Liquid melamine can be cooled, for example, by introducing solid melamine into liquid melamine which is under a certain ammonia pressure. The solid melamine is heated on introduction of and mixing with the melt, while the melt cools. The ammonia pressure under which the melt is can in this case remain the same, be increased or be decreased. Preferably, in a continuous process it remains roughly constant.

The temperature of the melt or of the resulting mixture can, if appropriate, be decreased with the aid of additional cooling to below the solidification point of melamine, so that pure and solid melamine is formed in a gentle manner. If appropriate, the solid melamine formed still remains for a certain time under ammonia pressure, and is then depressurized.

However, it is also possible to decrease the temperature of the liquid melamine to be cooled only to the melamine solidification point, dependent on the respective ammonia pressure, or to just above it, in which case it is possible to add to the solid melamine ammonia also, for instance in liquid, gaseous or supercritical state, to saturate with ammonia the liquid melamine which can absorb more ammonia at lower temperature. This procedure can also be used, for example, if the liquid $NH_3$-saturated melamine melt is then to be depressurized and solidified for instance in accordance with WO 97/20826.

The preferred possibility for cooling liquid melamine with solid melamine is to cool it below the solidification point.

It is possible in this case to mix the mixing partners, retaining the existing pressure, with subsequent pressure increase or under pressure decrease. Preferably, mixing is performed with pressure decrease.

It is possible to introduce solid melamine into liquid melamine or liquid melamine into solid melamine, or to introduce both mixing partners simultaneously into a quencher.

According to a preferred embodiment, solid melamine is charged into a vessel and liquid melamine is introduced, preferably with pressure decrease. Particularly preferably, the mixing is carried out in a fluidized bed.

At the beginning of the reaction, solid melamine or foreign material in the form of solid inert substances or a mixture of solid melamine and solid inert substances is introduced into the fluidized-bed reactor and used to build up the fluidized bed. As solid inert materials, use is preferably made of fluidizing bodies of metals or glass, for example balls or rods of steel, in particular stainless steel, steel alloys or titanium alloys. The fluidized bed is maintained by a gas, preferably ammonia. The temperature in the fluidized-bed reactor is below the melting point of melamine. Liquid melamine is injected. The finely divided liquid melamine forms a layer over the solid melamine particles or inert substance particles, causes these to grow and becomes solid. Owing to the agitation and friction of the particles in the fluidized bed, melamine is continuously abraded or knocked off from the particles. The larger and thus heavier melamine particles are discharged, for instance using a cyclone, as soon as they have reached a certain wanted particle size. Firstly, solid cold melamine can, to a small proportion, be fed continuously, so that the liquid melamine can deposit and solidify on it, secondly, depending on the mode of operating the fluidized-bed reactor and the other conditions prevailing in the fluidized bed, solid melamine particles form even in the gas space, which particles serve as crystallization nuclei and are covered with liquid melamine which then likewise solidifies. In this case, no solid melamine or virtually no solid melamine needs to be fed from the outside.

The solid melamine particles and inert substance particles in the fluidized bed can be cooled, and thus the desired temperature in the fluidized bed set, in a plurality of ways, for example by built-in cooling elements, by feeding solid cold melamine, by inert particles which, if appropriate, are ejected and, after external cooling, returned to the fluidized bed, by feeding cold liquid $NH_3$ or gaseous $NH_3$, by the temperature and rate of the gas stream which maintains the fluidized bed, and by the enthalpy of evaporation of the ammonia present in the liquid melamine.

Some of this ammonia is recirculated to cool and maintain the fluidized bed. The ammonia is cooled, preferably before being returned to the fluidized bed, and if appropriate is liquefied. The other portion of the ammonia released can, depending on the existing pressure in the fluidized bed, be returned to the melamine/urea process in the gaseous or liquid state. Here, a particular advantage of the process according to the invention is displayed, since no additional gas or ammonia not originating from the melamine/urea process is necessary to maintain the fluidized bed.

The temperature existing and maintained in the fluidized bed, depending on the procedure chosen, can fluctuate in a large range between room temperature and to just below the pressure-dependent melting point of melamine. It is, for example, from approximately 100 to approximately 340° C., preferably from approximately 200 to approximately 340° C., particularly preferably from approximately 280 to approximately 320° C.

The pressure existing in the fluidized-bed reactor can likewise fluctuate in a large range, depending on the procedure chosen. It can be from somewhat over 1 bar to just below the pressure of the melamine melt to be cooled.

Customarily, the pressure in the fluidized-bed reactor is between approximately 1.5 and approximately 100 bar, preferably between approximately 1.5 bar and 50 bar, particularly preferably between approximately 5 and 25 bar. Above a pressure of approximately 13 bar, the excess $NH_3$ gas can readily be liquefied and returned to the urea and melamine synthesis.

The $NH_3$ pressure above the melamine melt to be cooled can likewise vary in a large range. Frequently, it is at the pressure of the melamine synthesis carried out in the reactor. However, it can be substantially higher if an "aging" process is connected downstream of the melamine synthesis. The pressure can accordingly be up to 1000 bar or up to the limits which are economic and expedient and possible in terms of materials. On introducing the melamine melt into the fluidized-bed reactor, the pressure is reduced to that prevailing there, the liquid melamine being cooled and solidified. In principle, the temperature of the liquid melamine to be cooled can vary in a large range. It is above the melting point of melamine, dependent on the respective ammonia pressure, in a range up to approximately 450° C., preferably up to approximately 370° C., particularly preferably up to about 350° C. The higher the ammonia pressure, and the lower the temperature of the melamine melt, the more ammonia is present in the melamine, and the lower is the melting point. At an ammonia pressure of 300 bar, the melting point is, for example, at about 300° C., at 1 bar it is at 354° C. It is therefore also possible to have melamine liquid at 300° C. present, more precisely a mixture of liquid melamine with ammonia, and to depressurize it if the pressure is high enough. It is particularly advantageous to carry out depressurization at a temperature which is not essentially above the respective melting point of the melamine, and to mix it with the solid melamine. This cooling to just above the melting point of the melamine is preferably carried out by feeding cold liquid ammonia or gaseous or supercritical ammonia. The ammonia present in the liquid melamine likewise contributes to cooling in the subsequent depressurization and counteracts the enthalpy of melting released on solidification of the melamine.

If solid melamine is fed, the temperature of the solid melamine can be at any described value below the melting point of melamine, a greater temperature difference between solid melamine and liquid melamine to be cooled having a greater cooling effect. Advantageously, melamine fine contents produced can be returned to the fluidized-bed reactor, and serve there as crystallization nuclei.

A further possibility for temperature control is injecting liquid ammonia.

The temperature of the solid melamine to be discharged can be any value below the melting point of melamine, preferably it is below approximately 320° C., particularly preferably below about 300° C. The solid melamine, which can further be subjected as desired to a heat treatment under ammonia pressure (tempering) is then further depressurized and cooled to room temperature in any desired manner. During tempering, the liquid melamine is cooled to below the melting point which is dependent on the respective ammonia pressure and is then kept for approximately 1 min to 20 h under an ammonia pressure of from about 5 to 1000 bar at a temperature of approximately 100° C., preferably approximately 200° C., to below the melting point dependent on the respective ammonia pressure.

The process according to the invention is preferably carried out following a melamine synthesis from urea, particularly preferably following a melamine synthesis under pressure.

EXAMPLE

In a pilot plant, the melamine taken off from the reactor of a production plant is separated in a separator from the reaction gases (off-gases) $CO_2/NH_3$, stripped by 100 kg of ammonia/h in a downstream reaction vessel at a pressure of 100 bar and then passed into an aging vessel. At an $NH_3$ pressure of 250 bar and a temperature of 330° C., the melamine melt was saturated with $NH_3$ and allowed to dwell for one hour. From the aging vessel, then, approximately 11 kg of melamine melt/h were sprayed into a melamine fluidized bed. The fluidized bed was maintained by $NH_3$ gas and operated at a pressure of 25 bar at a temperature of 300° C. Solid melamine was discharged, depressurized and cooled to room temperature. Purity: 99.8% by weight melamine.

What is claimed is:

1. A process for cooling liquid melamine produced by reaction of urea and $NH_3$ which is under $NH_3$ pressure, which comprises introducing said liquid melamine into a fluidized bed, made up of solid melamine and/or solid inert substances, maintained by a gas, while depressurizing said liquid melamine, thereby cooling and solidifying said liquid melamine on said solid melamine and/or inert surfaces.

2. The process as claimed in claim 1, wherein the liquid melamine to be cooled is under an $NH_3$ pressure of 40–1000 bar.

3. The process as claimed in claim 1, wherein the liquid melamine to be cooled is under an $NH_3$ pressure of 40–400 bar.

4. The process as claimed in claim 1, wherein the liquid melamine to be cooled is under an $NH_3$ pressure of 40–300 bar.

5. The process as claimed in claim 1, wherein the temperature of the liquid melamine is from just above the melamine solidification point, dependent on the respective $NH_3$ pressure to 450° C.

6. The process as claimed in claim 1, wherein the temperature of the liquid melamine is from just above the melamine solidification point, dependent on the respective $NH_3$ pressure to 370° C.

7. The process as claimed in claim 1, wherein the temperature of the liquid melamine is from just above the melamine solidification point, dependent on the respective $NH_3$ pressure to 350° C.

8. The process as claimed in claim 1, wherein the liquid melamine is cooled prior to introduction of said liquid melamine into said fluidized bed and before depressurizing by addition of cold, liquid or gaseous or supercritical ammonia to a temperature just above the melting point of melamine.

9. The process as claimed in claim 1, wherein the temperature in the fluidized bed is from 100–340° C.

10. The process as claimed in claim 1, wherein the temperature in the fluidized bed is from 200–340° C.

11. The process as claimed in claim 1, wherein the temperature in the fluidized bed is from 280–320° C.

12. The process as claimed in claim 1, wherein the $NH_3$-pressure in the fluidized bed is from 1.5–100 bar.

13. The process as claimed in claim 1, wherein the $NH_3$-pressure in the fluidized bed is from 1.5–50 bar.

14. The process as claimed in claim 1, wherein the $NH_3$-pressure in the fluidized bed is from 5–25 bar.

15. The process as claimed in claim 1, wherein the cooling is performed by built-in cooling elements in said fluidized bed, by feeding solid, cold melamine, by inert particles, which, optionally, are ejected and, after external cooling, returned to the fluidized bed, by feeding cold liquid $NH_3$ or gaseous $NH_3$, by the temperature and rate of the gas stream, which maintains the fluidized bed, and by the enthalpy of evaporation of ammonia present in the liquid melamine.

16. The process as claimed in claim 1, wherein part of the present or released ammonia in the fluidized bed is recirculated and before recirculating, cooled and optionally liquified.

17. The process as claimed in claim 1, wherein part of the present or released ammonia in the fluidized bed is returned to the melamine/urea process in the gaseous or liquid state.

18. The process as claimed in claim 1, wherein the already solid melamine is kept below the melting point for approximately 1 minute to 20 hours under an ammonia pressure of from about 5 to 1000 bar at a temperature of approximately 100° C., to below the melting point dependent on the respective ammonia pressure.

19. The process as claimed in claim 1, wherein the already solid melamine is kept below the melting point for approximately 1 minute to 20 hours under an ammonia pressure of from about 5 to 1000 bar at a temperature of approximately 200° C., to below the melting point dependent on the respective ammonia pressure.

* * * * *